US006949099B2

United States Patent
Shiro et al.

(10) Patent No.: US 6,949,099 B2
(45) Date of Patent: Sep. 27, 2005

(54) INCISING DEVICE FOR USE WITH AN ENDOSCOPE

(75) Inventors: Chika Shiro, Hachioji (JP); Naohisa Yahagi, Tokyo (JP)

(73) Assignee: Olympus Corporation, Tokyo (JP)

(*) Notice: Subject to any disclaimer, the term of this patent is extended or adjusted under 35 U.S.C. 154(b) by 9 days.

(21) Appl. No.: 10/411,840

(22) Filed: Apr. 11, 2003

(65) Prior Publication Data

US 2004/0039249 A1 Feb. 26, 2004

(30) Foreign Application Priority Data

Apr. 12, 2002 (JP) ........................................ 2002-110243

(51) Int. Cl.$^7$ ............................................... A61B 18/14
(52) U.S. Cl. ........................................... 606/45; 606/46
(58) Field of Search ............................... 606/45, 27–39

(56) References Cited

U.S. PATENT DOCUMENTS

| 5,409,453 A | * | 4/1995 | Lundquist et al. | ............ 604/22 |
| 5,480,397 A | * | 1/1996 | Eggers et al. | .................. 606/29 |
| 5,593,406 A | * | 1/1997 | Eggers et al. | .................. 606/29 |
| 6,217,575 B1 | * | 4/2001 | DeVore et al. | ................. 606/41 |
| 6,423,060 B1 | * | 7/2002 | Ouchi | .......................... 606/41 |
| 6,494,881 B1 | * | 12/2002 | Bales et al. | .................... 606/45 |

FOREIGN PATENT DOCUMENTS

JP          61-191012          11/1986

* cited by examiner

Primary Examiner—Henry M Johnson, III
(74) Attorney, Agent, or Firm—Scully, Scott, Murphy & Presser (57) ABSTRACT

In an incising device for use with endoscope having an electrode 3 for incising an organic tissue on its distal end and an energy connecting portion on it proximal end portion, the electrode 3 is formed of a pliable member having flexibility.

11 Claims, 6 Drawing Sheets

FIG. 13

INCISING DEVICE FOR USE WITH AN ENDOSCOPE

CROSS-REFERENCE TO RELATED APPLICATIONS

This application is based upon and claims the benefit of priority from the prior Japanese Patent Application No. 2002-110243, filed Apr. 12, 2002, the entire contents of which are incorporated herein by reference.

BACKGROUND OF THE INVENTION

1. Field of the Invention

The present invention relates to an incising device for use with endoscope, to be inserted into a patient's body through an endoscope and subject an organic tissue, such as a mucous membrane, to energy incision.

2. Description of the Related Art

Conventionally described in Jpn. UM Appln. KOKAI Publication No. 61-191012, for example, is a high-frequency instrument to be inserted into the body cavity through an endoscope and excise a mucosal part in a wide range in the body cavity. This high-frequency instrument comprises an electrically conductive sheath, a tip member attached to the distal end portion of the sheath, and a control wire passed through the sheath. The sheath can be passed through a channel of the endoscope. The control wire has, on its distal end portion, a knife that can project and recede from the tip member.

The knife is a rod-shaped member, which is formed of a single wire having a pointed end, or a member in the form of a thin sheet. As the knife is supplied with high-frequency current and heated, it can subject a tissue to high-frequency incision. Alternatively, a wire may be used to subject a region around an affected part of a mucous membrane in a wide range to high-frequency incision. In this case, a submucosa is exfoliated to be excised by means of this high-frequency incision tool.

As is generally known, a high-frequency snare is used endoscopically to excise polyps or mucous membranes. This high-frequency snare comprises an electrically conductive sheath, an incision wire passed through the sheath, and a slider. The sheath can be passed through a channel of an endoscope. The slider is slidably mounted on the proximal portion of the incision wire.

As the slider is advanced by means of a handle, in this high-frequency snare, the incision wire projects from the distal end of the sheath and spreads in a loop, undergoing restorative deformation. Originally, in this high-frequency snare, the incision wire is spread in a loop. In this state, the incision wire is hooked on an affected part, and the slider is retreated. The incision wire is drawn into the sheath to a degree such that the affected part touches the sheath, and the affected part is bound.

In excising a mucous membrane in a wide range, according to an alternative method of use of the high-frequency snare, the incision wire is projected about 1 mm from the sheath as it is supplied with high-frequency current. By doing this, the wire can be heated to subject a tissue to high-frequency incision. Thus, the incision wire can be used to mark the region around the affected mucosal part in a wider range, effect high-frequency incision, or exfoliate a submucosa.

BRIEF SUMMARY OF THE INVENTION

An incising device for use with an endoscope according to an aspect of the invention comprises: an electrically insulating tube having an extreme end portion and a through channel; an elongate control member passed through the channel of the tube and having a distal end portion and a proximal end portion; and an electrode connected to the distal end portion of the control member and capable of projecting and receding from the extreme end portion of the tube, the electrode being formed of a substantially rod-shaped pliable member having flexibility.

Objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate of the invention, and together with the general description given above and the detailed description of the embodiments given below, serve to explain the principles of the invention.

FIGS. 2A and 2B show the same embodiment, in which

FIGS. 3A and 3B show the same embodiment, in which

DETAILED DESCRIPTION OF THE INVENTION

Embodiments of the present invention will now be described with reference to the drawings.

Figure 1:
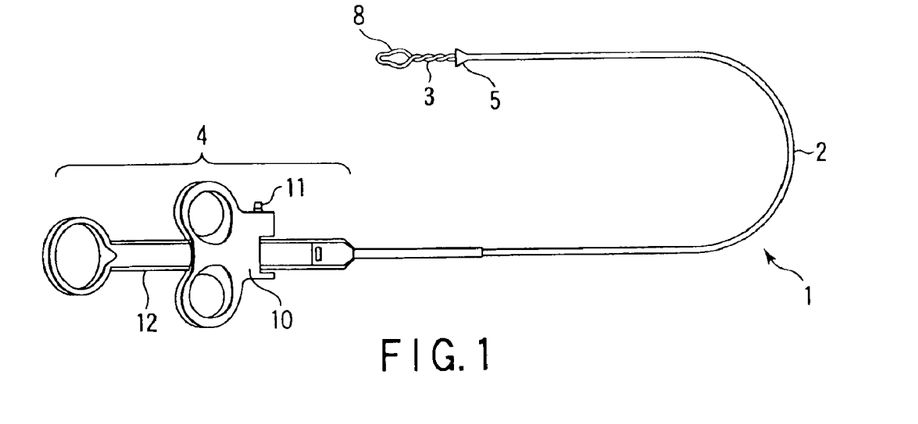
FIG. 1 is a general perspective view of a high-frequency instrument according to a first embodiment of the invention.
Figure 2A:
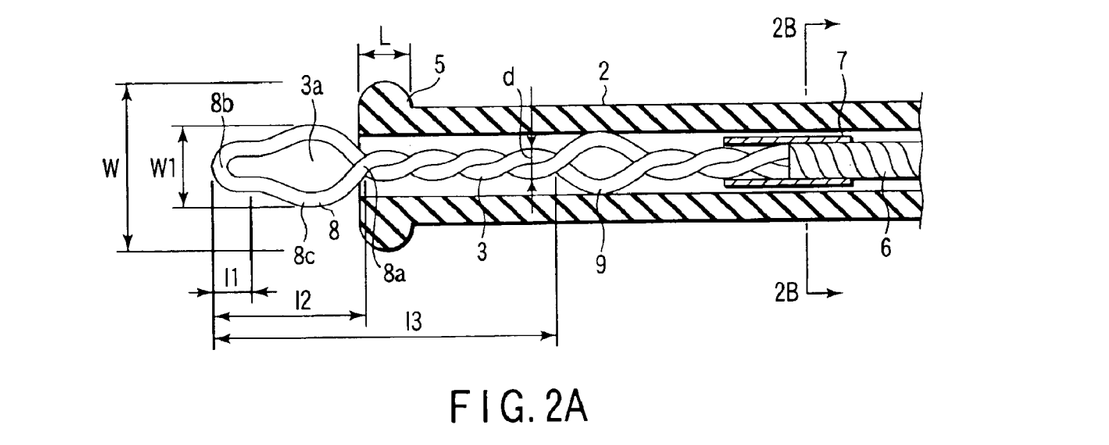
FIG. 2A is a longitudinal sectional side view of the distal end portion of an insert section.
Figure 2B:
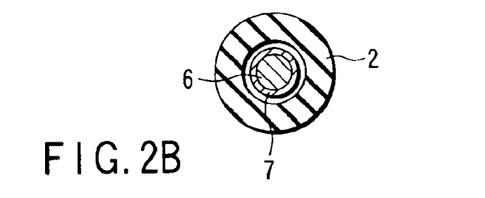
FIG. 2B is a sectional view taken along line 2B—2B of FIG. 2A.
Figure 3A:
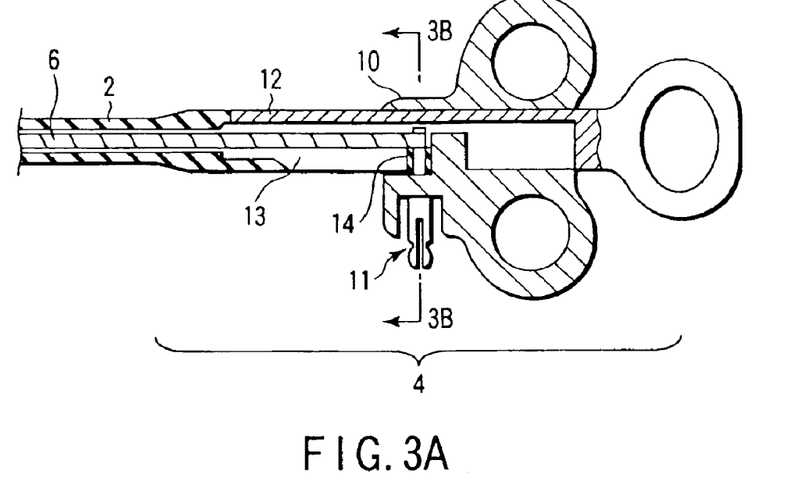
FIG. 3A is a longitudinal sectional view of a control section.
Figure 3B:
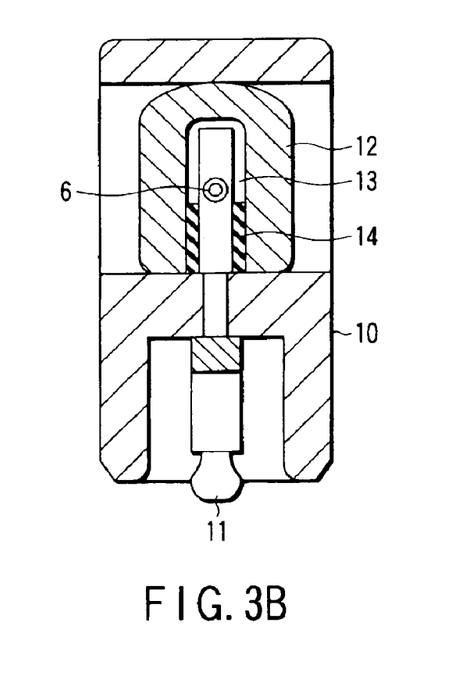
FIG. 3B is a sectional view taken along line 3B—3B of FIG. 3A.
Figure 4:
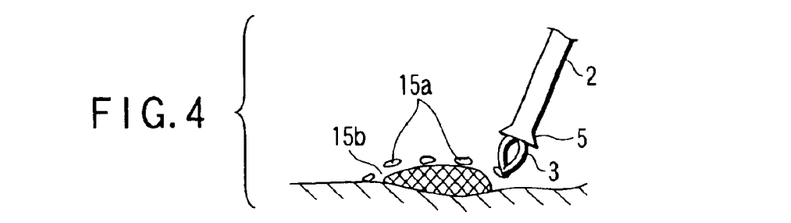
FIG. 4 is a perspective view showing the way of treatment by means of the high-frequency instrument according to the same embodiment.
Figure 5:
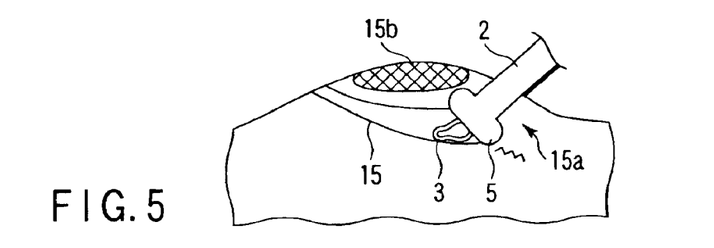
FIG. 5 is a perspective view showing the way of treatment by means of the high-frequency instrument according to the same embodiment.
Figure 6:
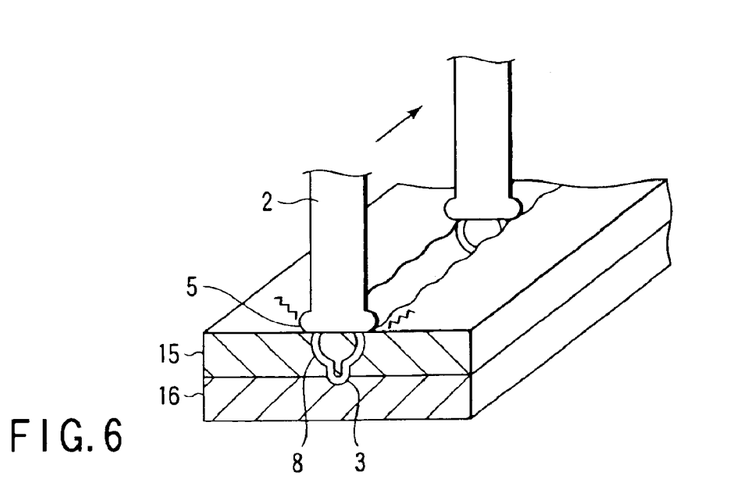
FIG. 6 is a perspective view showing the way of treatment by means of the high-frequency instrument according to the same embodiment.
Figure 7:
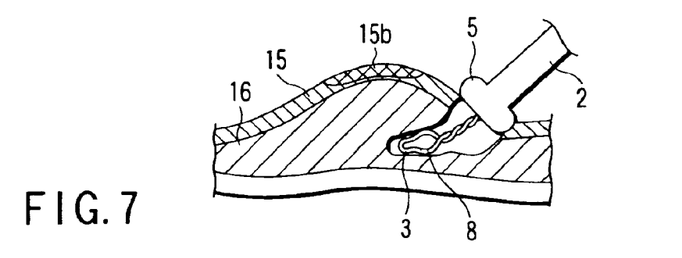
FIG. 7 is a perspective view showing the way of treatment by means of the high-frequency instrument according to the same embodiment.

FIGS. 1 to 7 show a first embodiment. FIG. 1 is a general perspective view of a high-frequency instrument for use as an incising device for use with endoscope. FIG. 2A is a longitudinal sectional side view of the distal end portion of an insert section. FIG. 2B is a sectional view taken along line 2B—2B of FIG. 2A. FIG. 3A is a longitudinal sectional side view of a control section. FIG. 3B is a sectional view taken along line 3B—3B of FIG. 3A. FIGS. 4 and 5 are perspective views showing the way of treatment. FIG. 6 is a perspective view showing the way of treatment. FIG. 7 is a sectional view showing the way of treatment.

As shown in FIG. 1, the high-frequency instrument 1 comprises a flexible sheath 2, an electrically conductive electrode 3, and a control section 4. The sheath 2 serves as an insert section that is passed through a channel of an endoscope (not shown). The electrode 3 is passed through the distal end portion of the sheath 2 and can project from the distal end face. The control section 4 is provided on the proximal end portion of the sheath 2.

The sheath 2 is composed of a flexible, electrically insulating PTFE or FEP tube, which has an outside diameter of, preferably, φ1.7 mm such that it can be passed through the channel of the endoscope and a wall thickness of 0.35 mm. The sheath 2 has a channel through which a control wire (mentioned later) is passed.

As shown in FIG. 2A, an expanded portion 5 is provided on the distal end portion of the sheath 2 of the high-frequency instrument 1. It has an increased outside diameter that is obtained by thermoforming the tube. Preferably, an axial distance L of the expanded portion 5 from the extreme end of the sheath 2 and a width W of the expanded portion 5 are L=1 mm and W=φ2.3 mm, respectively. The width (outside diameter) W of the expanded portion 5 is set to a value such that the electrode 3 that projects from the sheath 2 can be recognized as an endoscopic image. The electrode 3 is connected electrically and mechanically to the distal end portion of a control member or control wire 6, which is formed of an electrically conductive metallic wire. The proximal end of the wire 6 is connected to the control section 4. The electrode 3 is connected by spreading a connecting pipe 7 on its outer periphery or by brazing the pipe to it. The electrode 3 is formed of an electrically conductive material, such as stainless steel or other metal. It is formed by doubling one stranded wire with an outside diameter of φ0.15 mm to φ0.6 mm and twisting the doubled wire. More specifically, the electrode has a first portion, a second portion, and a turn portion that continuously extends between those portions. The first and second portions are intertwined with each other to form an intertwined portion. The material of the electrode 3 is a stranded wire obtained by braiding 19 stainless-steel strands with an outside diameter of φ0.06 mm or a stranded wire obtained by braiding 7 stainless-steel strands with an outside diameter of φ0.1 mm. The turn portion of the electrode 3 is curvedly turned back in a loop without being twisted, thereby forming a first outspread portion 8 that has a gap 3a between its linear wire portions. The first outspread portion 8 is composed of a smaller outspread section 8b on the distal end side and a larger outspread section 8c on the proximal end side. The length of the smaller outspread section, that is, a distance 11 from the extreme end of the first outspread portion 8 to the larger outspread section 8c, is 11=0.5 mm to 1.5 mm, and preferably, 11=0.5 mm. The proximal end portion of the first outspread portion 8 and the larger outspread section 8c is provided with a neck portion 8a. The distance from the extreme end of the electrode 3 to the neck portion 8a, that is, a length 12 of the first outspread portion 8, is 12=1.0 mm to 2.0 mm, and preferably, 12=1.5 mm.

If the maximum outside diameter of the twisted portion or shaft portion of the electrode 3 is d, a width W1 of the first outspread portion 8 is given by d+0.5≦W1≦2.0, and preferably, W1=1.2 mm. The electrode 3 is formed having an engaging portion or second outspread portion 9 at its proximal end portion that never projects from the tube and adjoins the distal end portion that can project from the tube. The second outspread portion 9 elastically engages the inner peripheral surface of the sheath. The second outspread portion 9 has elasticity such that it can extend and contract in the radial direction. In a natural state, it has its maximum outside diameter or a width that is greater than the inside diameter of the sheath 2. Preferably, this width is about 1.2 mm. The second outspread portion 9 is located on the distal end side of the sheath 2. It is set within a range such that it can be held in the sheath 2 even when a control slider 10 is moved toward the distal end so that the electrode 3 projects farthest from the distal end of the sheath 2. More specifically, the second outspread portion 9 is arranged so that its front end is situated in a position at a distance 13 of 5 to 10 mm, and preferably 6 mm, from the extreme end of the electrode 3.

As shown in FIG. 3A, the proximal end portion of the control wire 6 is coupled to the control slider 10 provided on the control section 4. The electrode 3 can be caused to project or recede from the distal end portion of the sheath 2 by forwardly or backwardly moving the control slider 10. The control slider 10 is provided with a connector port 11 to be connected electrically with a cord (not shown) that leads to a high-frequency generator (not shown). The length of the electrode 3 and the stroke of the control slider 10 are so set that the electrode 3 can project by about 5 mm from the distal end of the sheath 2.

In FIGS. 2A and 2B, the sheath 2 and the connecting pipe 7 are shown to be somewhat spaced, in order to discriminate clearly between them. The inside diameter of the distal end of the sheath 2 is substantially equal to the outside diameter of the connecting pipe 7, and these two members are substantially in contact with each other. In consequence, the connecting pipe 7, like the second outspread portion 9, functions as an engaging member that prevents unnecessary axial movement of the operating electrode, as mentioned before. The control section 4 is constructed by the control slider 10 and a control section body 12. The control section body 12 is provided with a groove 13 along which the control slider 10 slides in its axial direction. That part of the control slider 10 which is situated in the groove 13 is covered by a tube 14 of an elastic material, such as silicone, having an outside diameter a little greater than the width of the groove 13.

The following is a description of the operation of the apparatus of the first embodiment.

If the control slider 10 in the control section 4 of the high-frequency instrument 1 is advanced with respect to the control section body, the electrode 3 projects from the distal end of the sheath 2. The length of this projection can be controlled by means of the control slider 10. If the control slider 10 is retreated, in contrast with this, the electrode 3 can be held entirely in the sheath 2.

The sheath 2 of the high-frequency instrument 1 is passed through the channel of the endoscope and inserted into the body cavity through the endoscope. When the sheath 2 is to be inserted into the channel of the endoscope and the body cavity, the electrode 3 is retracted in the sheath 2.

As shown in FIG. 4, the control slider 10 is advanced to cause the electrode 3 to project from the distal end of the sheath 2. At the same time, high-frequency current is supplied to the electrode 3 so that the electrode 3 supplies current to regions that surround an affected mucosal part 15b to be incised, thereby effecting high-frequency marking. As this is done, the electrode 3 is expected only to touch the mucous membrane, so that it is projected slightly or by about 1 mm (first projection position), for example, in use. In FIG. 4, numeral 15a denotes marking.

Then, the sheath 2 of the high-frequency instrument 1 is temporarily removed from the channel of the endoscope, and an injection needle is introduced into the body cavity through the endoscope channel. A local injection (e.g., hypertonic salt solution, hypertonic glucose injection, sodium hyaluronate solution, etc.) is injected into a submucosa 16 of a mucosal part 15 to be incised. By doing this, the submucosa 16 is bulged, and the overlying affected mucosal part 15b is fully raised with respect to other parts. Thereafter, the sheath 2 of the high-frequency instrument 1 is inserted in place of the injection needle into the channel of the endoscope. It is guided to a target region to incise the mucosal part 15 around the affected mucosal part 15b. As this is done, the electrode 3 is projected slightly or by about 1 to 2 mm (second projection position), for example, from the distal end of the sheath 2, and the sheath 2 and the electrode 3 are pressed against the mucosal part 15. When this is done, the electrode 3 bends and faces the mucosal part 15 substantially in parallel relation. In this state, high-frequency current is supplied as the electrode 3 is moved, whereby the mucosal part 15 is incised around the affected mucosal part 15b. If the electrode 3 slips on the mucous membrane and fails to incise the mucous membrane, the mucosal part 15 is held between the larger outspread section 8c of the first outspread portion 8 and the distal end face of the sheath 2 and incised, as shown in FIG. 6. Thereafter, mucosal high-frequency current is supplied to the first outspread portion 8 as the electrode 3 is moved around the affected mucosal part 15b. When this is done, the electrode 3 is projected substantially or by about 3 to 5 mm (third position), for example, from the distal end of the sheath 2 so that the distal end side of the electrode 3 is situated in the submucosa 16 under the affected mucosal part 15b, as shown in FIG. 7. In consequence, that part of the submucosa 16 which carries the affected mucosal part 15b thereon can be exfoliated and excised. In this case, the length of projection of the electrode 3 from the sheath 2 is suitably adjusted in use, depending on the distance between the endoscope and the lesion, and the shape as well as size of the lesion.

For the treatment described above, as shown in FIGS. 6 and 7, the expanded portion 5 is provided on the distal end of the sheath 2. Therefore, the expanded portion 5 abuts against the surface layer of the mucosal part 15 and serves as a stopper. Thus, the sheath 2 itself never gets in deep under the mucosal part 15, so that the depth of incision can be controlled.

In projecting the electrode 3 from the sheath 2 to effect marking, incision of the mucous membrane, or exfoliation of the submucosa, the second outspread portion 9 prevents the electrode 3 from being pushed into the sheath 2, by frictional engagement with the inner peripheral surface of the sheath 2. Thus, the length of projection of the electrode 3 can be fixed.

Since the second outspread portion 9 is located on the distal end side of the sheath 2, the distance from the second outspread portion 9 fixed to the sheath 2 to the first outspread portion 8 is short. Therefore, that part of the wire on the distal end side of the second outspread portion 9 is hardly slack. Thus, the length of projection of the electrode 3 can be kept fixed more securely.

According to the first embodiment, the sheath 2 and the electrode 3 are pliable when the high-frequency instrument 1 effects high-frequency marking around the mucosal part 15 or incision. When they are pressed against the mucosal part 15, therefore, the electrode 3 bends and extends parallel to the mucosal part 15. Thus, the electrode 3 can easily incise and exfoliate the mucosal part 15 without the possibility of cutting deep into it.

If the same pliability is obtained with use of a prior art electrode that is formed of a single wire, the diameter of the wire must be reduced extremely, so that heat that is produced during the incision makes the wire fragile. If the stranded wire is used, however, the pliability can be enjoyed without failing to maintain satisfactory durability.

As shown in FIG. 6, the expanded portion 5 at the distal end of the sheath 2 abuts against the surface layer of the mucosal part 15 and serves as a stopper. When the mucosal part 15 is incised, therefore, the sheath 2 does not insert into the mucosal part 15, so that the depth of incision in the mucosal part 15 can be controlled. If the outside diameter of the sheath is uniformly increased throughout the length of the sheath, as in the conventional case, the gap between the sheath and the inner surface of the endoscope channel is reduced along the entire length of the channel when the sheath is inserted through the channel, so that the sucking function through the endoscope channel (i.e., the gap) of a conventional endoscope is inevitably lowered. However, the sucking function cannot be directly damaged if only the distal end of the sheath 2 is enlarged as described above.

Since the expanded portion 5 is located within about 1 mm (has a length of less than 1 mm) from the distal end of the sheath 2, the flexibility of the distal end portion (having a length much longer than 1 mm) of the sheath 2 cannot be ruined, so that the operating efficiency cannot be lowered.

By turning and twisting the electrode 3, moreover, the pliable electrode 3 having the first and second outspread portions 8 and 9 can be constructed with ease. The inside diameter of the distal end of the sheath 2 and outside diameter of the connecting pipe 7 are substantially equal, so that the electrode 3 in the sheath 2 is subject to no play. Thus, the operation of the electrode 3 is facilitated, so that manipulation for incision, exfoliation, etc. is easy.

Under frictional resistance between the sheath 2 and the second outspread portion 9, moreover, the second outspread portion 9 can frictionally engage the inside portion of the sheath 2, thereby preventing the electrode 3 from projecting or receding unexpectedly. Since the silicone tube 14 is provided to the control slider 10, furthermore, frictional resistance acts on the control slider 10 and the groove 13 of the control section body 12, so that the position of the control slider 10 is fixed. Thus, if the control slider 10 is released from hold, therefore, the length of projection of the electrode 3 can be fixed according to the depth or purpose.

Further, the electrode 3 is provided with the first outspread portion 8. As the mucosal part 15 is incised, the mucous membrane of the mucosal part 15 is caught by the neck portion 8a of the electrode 3 and the distal end portion of the sheath 2. Thus, the electrode 3 can be prevented from unexpectedly slipping out of the mucosal part 15, so that incision can be carried out smoothly. If the width W1 of the first outspread portion 8 is too large, the first outspread portion 8 cannot be easily inserted into a shallow cut formed on the surface of the mucasal part 15 when the mucous membrane is incised. If the width W1 of the first outspread portion 8 is too small, the electrode 3 slips off as the mucous membrane is incised, so that smooth incision is impossible. Furthermore, the one high-frequency instrument can achieve a series of manipulations for marking, mucous membrane incision, and submucosa exfoliation. Furthermore, the one high-frequency instrument can achieve a series of manipulations for marking, mucous membrane incision, and submucosa exfoliation.

Figure 8:
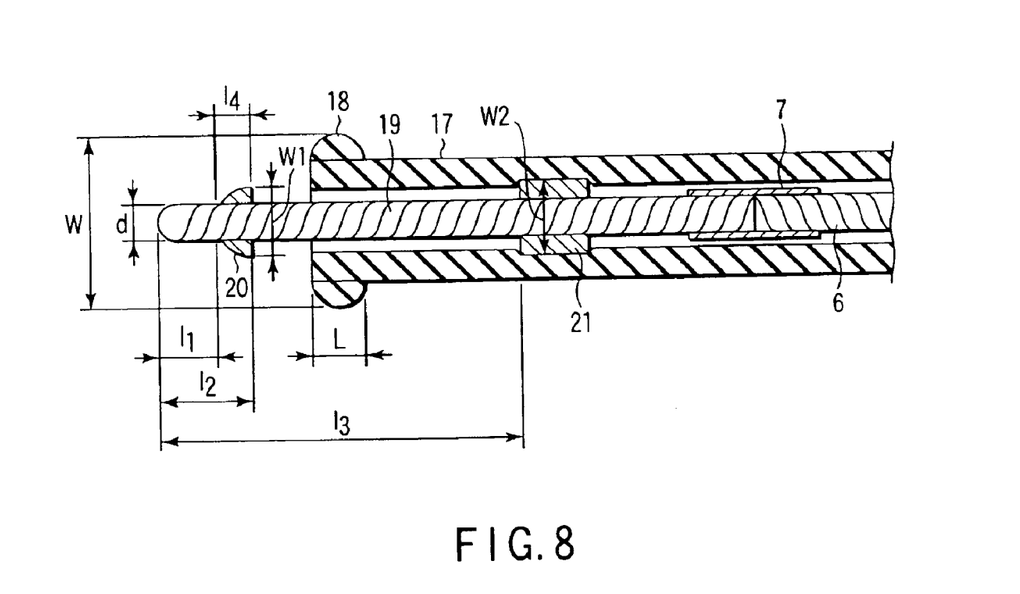
FIG. 8 is a longitudinal sectional side view of the distal end portion of an insert section according to a second embodiment of the invention.

FIG. 8 is a longitudinal sectional side view of the distal end portion of an insert section, and shows a second embodiment. A sheath 17 of the present embodiment is composed of a pliable, electrically insulating PTFE or FEP tube, which has an outside diameter such that it can be passed through the channel of the endoscope and a wall thickness that ensures proper elasticity of the sheath. Preferably, the diameter and the wall thickness are φ1.7 mm and 0.35 mm, respectively.

An expanded portion 18 is formed in a manner such that an FEP tube having an inside diameter substantially equal to the outside diameter of the sheath 17 is thermally welded or bonded thereto, covering a length L of about 1 mm from the extreme end portion of an electrode 19. An outside diameter W of the expanded portion 18 is about φ2.3 mm. Further, the electrode 19 is composed of a stranded wire of an electrically conductive material, such as stainless steel, having an outside diameter of φ0.4 mm to φ0.6 mm. The stranded wire that is used as the material of the electrode 19 is obtained by braiding 7 strands with an outside diameter of φ0.1 mm. A first outspread portion 20 is provided on the electrode 19. A position 11 of the first outspread portion 20 or its distance from the distal end of the electrode 19 is about 0.5 mm to 1.0 mm, and preferably, 0.5 mm.

The first outspread portion 20 is so formed that a stainless-steel pipe with an inside diameter substantially equal to the outside diameter of the electrode 19 is fixed on the electrode by caulking or brazing. A length 14 of the first outspread portion 20 is 14=0.5 mm to 1.0 mm, while the outside diameter W is 0.5 mm larger than that of a shaft d of the electrode 19. The maximum outside diameter is 2 mm or less. A second outspread portion 21 is provided on the rear side of the first outspread portion 20. A position 13 of the second outspread portion 21 or its distance from the distal end of the electrode 19 ranges from 2 mm to 4 mm. An outside diameter W2 of the second outspread portion 21 is larger than the inside diameter of the sheath 17, and preferably ranges from 1.0 mm to 1.2 mm. The second embodiment shares other configurations with the first embodiment.

According to the second embodiment, the stainless-steel pipe is provided with the expanded portion 18 of the sheath 17, electrode 19 formed of one stranded wire, and first outspread portion 20, and produces the same effect of the first embodiment. The diameter of the second outspread portion 21 is larger than the inside-diameter of the sheath 17. When the electrode 19 is advanced or retreated, therefore, frictional resistance with the sheath 17 can prevent the electrode 19 from projecting or receding unexpectedly.

Figure 9:
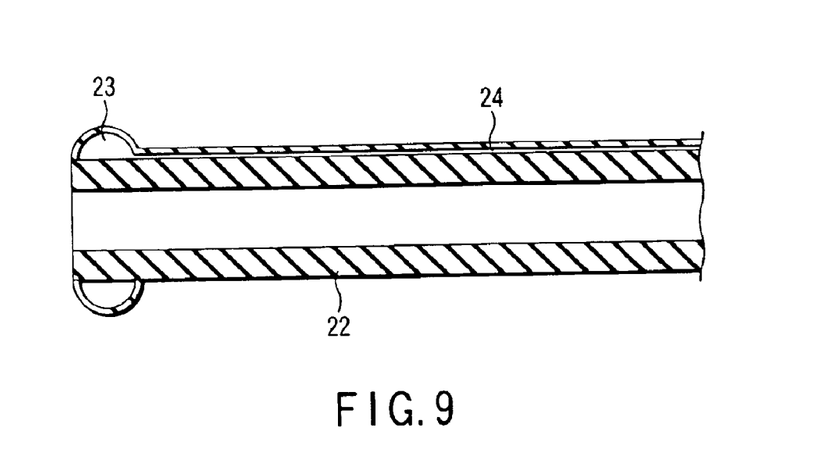
FIG. 9 is a longitudinal sectional side view of the distal end portion of an insert section according to a third embodiment of the invention.

FIG. 9 is a longitudinal sectional side view of the distal end portion of an insert section, and shows a third embodiment. A sheath 22 of the present embodiment is identical with that of the first embodiment. The sheath 22 is a PTFE tube that has an inside diameter of φ1 mm and an outside diameter of φ1.7 mm. The extreme end portion of the sheath 22 is provided with a balloon 23 that spreads to φ2.3 mm. The balloon 23 is connected to a feed air line 24. The feed air line 24 extends along the endoscope to the control section. The third embodiment shares other configurations with the first embodiment.

In use, according to the third embodiment, the balloon 23 is normally inflated with air that is introduced into the balloon 23 through the feed air line 24. The balloon 23 functions as a stopper when the mucous membrane is incised. In cutting deep into the mucous membrane, air in the balloon 23 is sucked out through the feed air line 24 lest the balloon 23 function as a stopper.

According to the third embodiment, the distal end portion of the sheath can be caused alternatively to get in place, and various methods may be used for the incision. The third embodiment shares other effects with the first embodiment.

Figure 10:
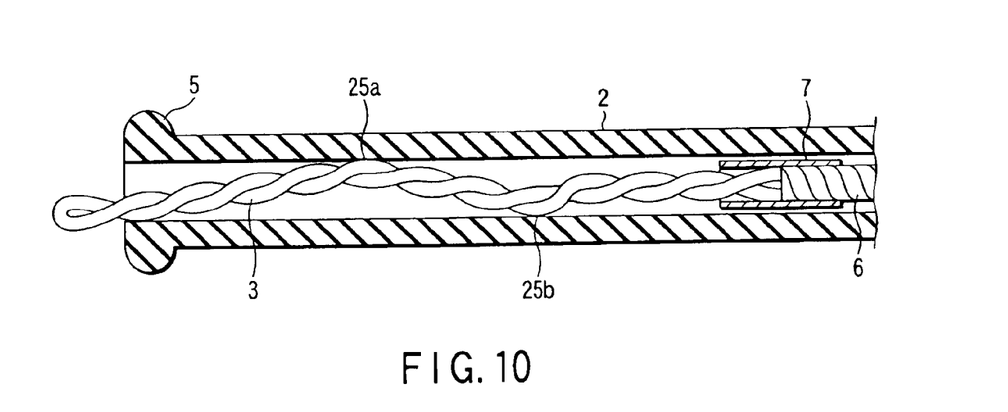
FIG. 10 is a sectional view showing a part of an incising device for use with endoscope according to a fourth embodiment of the invention.
Figure 11:
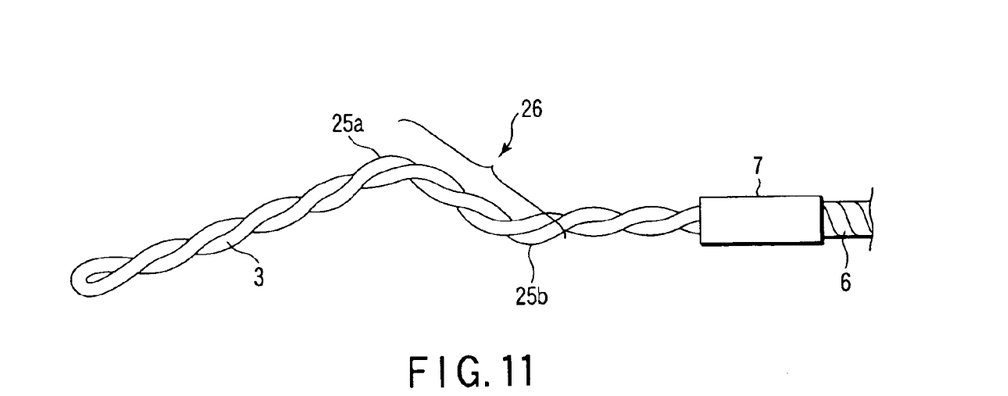
FIG. 11 is a side view showing an electrode of the incision tool shown in FIG. 10.

FIGS. 10 and 11 show a fourth embodiment. FIG. 10 is a longitudinal sectional view of the distal end portion of an insert section, and FIG. 11 is a side view showing an electrode 3 only. The electrode 3 of the present embodiment, like that of the first embodiment, is formed by turning a stranded wire and intertwining the other parts of the turned wire than its distal end portion. The distal end portion of the electrode 3 has a diameter substantially equal to that of the intertwined portion on the proximal end side. Further, that part of the electrode 3 which is situated in a sheath 2 without projecting from it is provided with two bent portions 25a and 25b, which form an engaging portion 26 having a diameter larger than the inside diameter of the sheath 2. The fourth embodiment shares other configurations with the first embodiment.

According to the fourth embodiment, the engaging portion 26 is formed by providing the electrode 3 with the bent portions 25a and 25b, so that the engaging portion 26 can be formed having a simple construction.

Figure 12:
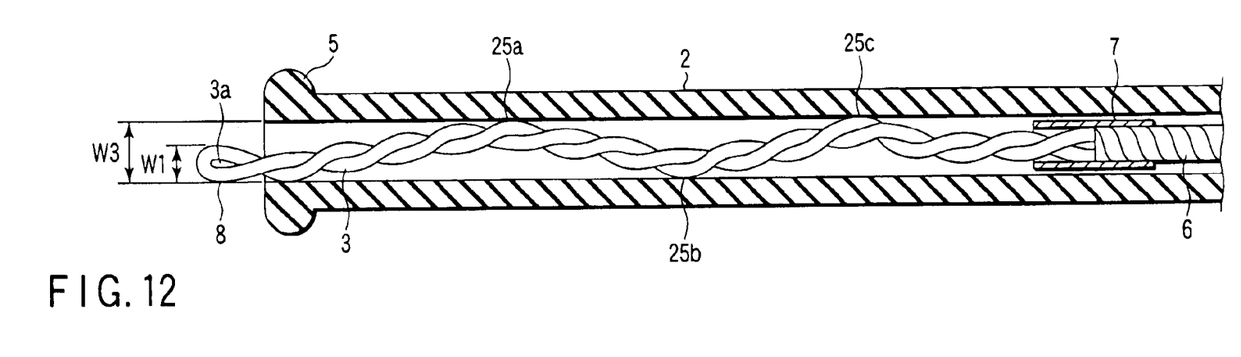
FIG. 12 is a sectional view showing a part of an incising device for use with endoscope according to a fifth embodiment of the invention.
Figure 13:
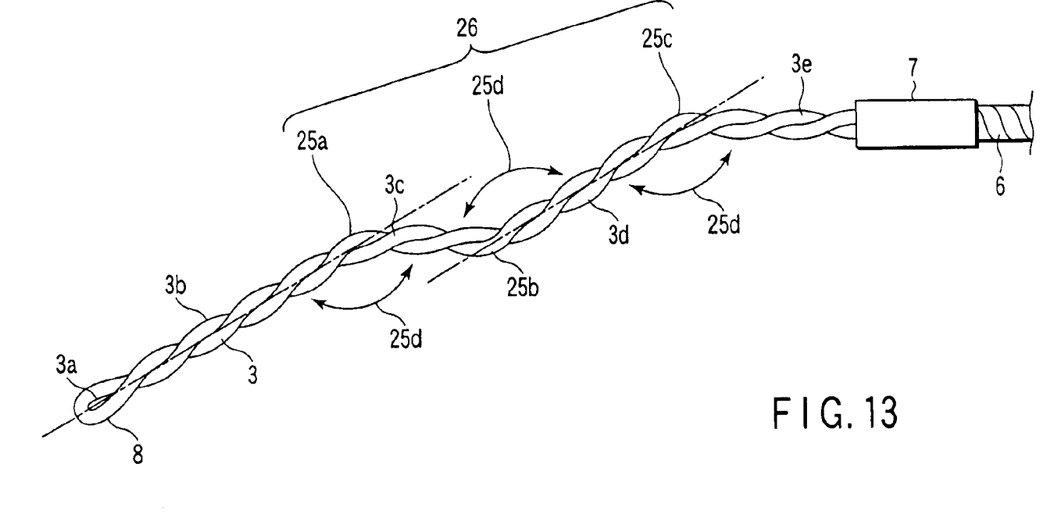
FIG. 13 is a side view showing an electrode of the incision tool shown in FIG. 12.

FIGS. 12 and 13 show a fifth embodiment. FIG. 12 is a longitudinal sectional side view of the distal end portion of an insert section. FIG. 13 is a side view showing an electrode 3 only. The electrode 3 of the present embodiment, like that of the first embodiment, is formed by turning a stranded wire and twisting the turned wire. The distal end portion of the electrode 3 is provided with a substantially loop-shaped first outspread portion 8, which has a gap 3a in the twisted portion of the wire. The width W1 of the first outspread portion 8 is smaller than an inside diameter W3 of a sheath 2. Further, that part of the electrode 3 which is situated in the sheath 2 without projecting from it is provided with three bent portions 25a, 25b and 25c, which form an engaging portion 26 (second outspread portion 9) having a diameter larger than the inside diameter of the sheath 2. Thus, the electrode 3 forms four sides 3b, 3c, 3d and 3e. The bent portions 25 are arranged so that the sides 3b and 3c extend parallel to the sides 3d and 3e, respectively, that is, the bent portions 25 are bent at the same angle 25d. The fifth embodiment shares other configurations with the first embodiment.

According to the fifth embodiment, the bent portions 25 that form the engaging portion 26 are arranged so that they are bent at the same angle 25d. Thus, the operation to form the engaging portion 26 is easy.

Since the diameter of the first outspread portion 8 is smaller than the inside diameter of the sheath 2, moreover, the electrode 3 can be caused to project or recede from the sheath 2 with a small force.

The electrode 3 is not limited to the examples according to the first to fifth embodiments. It is necessary only that it be a substantially rod-shaped electrode that is formed by turning a stranded wire and twisting the turned wire.

The following tools are obtained according to the embodiments described above.

1. In an incising device for use with endoscope having an electrode for incising an organic tissue on its distal end and an energy connecting portion on it proximal end portion, the electrode is formed of a pliable member having flexibility.

2. In the incising device for use with endoscope as described in paragraph 1, the electrode is a substantially rod-shaped structure formed of two or more intertwined wires.

3. In the incising device for use with endoscope as described in paragraph 1, the electrode is provided with at least one expanded portion.

4. In the incising device for use with endoscope as described in paragraph 1, an electrically conductive member is located on the proximal side of the electrode, the extreme end portion of the member having an increased outside diameter.

5. In the incising device for use with endoscope as described in paragraph 1, the incision tool comprises an electrically insulating tube, a control member passed through the tube, and an electrode connected to the distal end of the control member, the electrode being capable of projecting and receding from the distal end of the tube, the incision tool further comprising an engaging portion located in at least one place in a range such that the engaging portion never projects from the electrode or the tube of the control member and capable of engaging the inner surface of the tube.

6. In the incising device for use with endoscope as described in paragraph 3, the maximum width of the electrode is 2 mm or less.

7. In the incising device for use with endoscope as described in paragraph 3, the expanded portion of the electrode is located at a distance of 0.5 mm to 1.5 mm from the distal end.

8. In the incising device for use with endoscope as described in any one of paragraphs 3, 6 and 7, the electrode is a substantially rod-shaped structure formed of two or more intertwined wires, and the expanded portion is formed by bending at least one of the wires that constitute the electrode.

9. In the incising device for use with endoscope as described in paragraph 4, the incision tool comprises an electrically insulating tube, a control member passed through the tube, and an electrode connected to the distal end of the control member, the electrode being capable of projecting and receding from the distal end of the tube, the extreme end portion of the tube having an increased outside diameter.

10. In the incising device for use with endoscope as described in paragraph 5, the maximum width of the engaging portion is larger than the inside diameter of the tube.

11. In the incising device for use with endoscope as described in paragraph 5 or 11, the engaging portion is formed of at least one wire.

12. In the incising device for use with endoscope as described in paragraph 11, the electrode is a substantially rod-shaped structure formed of two or more intertwined wires, and the engaging portion is formed of at least one of the wires that constitute the electrode.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An incising device for use with endoscope comprising:
   an electrically insulating tube having an extreme end portion and a through channel;
   an elongate control member passed through the channel of the tube and having a distal end portion and a proximal end portion;
   an electrode connected to the distal end portion of the control member and capable of projecting from the extreme end portion of the tube, the electrode being formed of a substantially rod-shaped pliable member having flexibility; and
   an engaging portion located in at least one place on the electrode or the control member in a range such that the engaging portion never projects from the electrode or the tube of the control member, having a width longer than the diameter of the inner peripheral surface of the tube defining the channel, and capable of frictionally engaging the inner peripheral surface of the tube.

2. An incising device for use with endoscope according to claim 1, wherein the extreme end portion of the tube has an expanded portion larger than any other portions in outside diameter.

3. An incising device for use with endoscope according to claim 2, wherein the length of the expanded portion of the tube in the length direction of the tube is about 1 mm.

4. An incising device for use with endoscope according to claim 1, wherein the engaging portion is provided on the electrode so as to be situated close the extreme end portion of the tube.

5. An incising device for use with endoscope according to claim 1, wherein the engaging portion has elasticity.

6. An incising device for use with endoscope according to claim 1, wherein the engaging portion has at least one bent portion formed on a part of the electrode.

7. An incising device for use with endoscope according to claim 1, wherein the electrode has a first portion, a second portion, and a turn portion continuously extending between the first and second portions and forming the distal end portion of the electrode, the first and second portions being intertwined with each other to form an intertwined portion.

8. An incising device for use with endoscope according to claim 7, wherein the distal end turn portion of the electrode has a diameter larger than that of the intertwined portion and smaller than an outside diameter of the tube.

9. An incising device for use with endoscope comprising:
   an electrically insulating tube having an extreme end portion with an opening;
   an electrically conductive, flexible elongate control member inserted in the tube for movement in the tube and having a distal end portion; and
   an electrode connected electrically and mechanically to the distal end portion of the control member and capable of projecting and receding from the opening of the extreme end portion of the tube, the electrode having an intertwined portion formed of one twisted wire;
   wherein the intertwined portion has a distal end portion projecting from the tube and a proximal end portion adjoining the distal end portion and held in the tube, the proximal end portion having an engaging portion which elastically engages an inner peripheral surface of the tube, thereby preventing the distal end portion projected from the tube from returning to the interior of the tube during use.

10. An incising device for use with endoscope according to claim 9, wherein the distal end portion of the electrode is deformable when projected from the tube.

11. An incising device for use with endoscope comprising:
    an electrically insulating tube having an extreme end portion and a through channel;
    an elongate control member passed through the channel of the tube and having a distal end portion and a proximal end portion; and
    an electrode connected to the distal end portion of the control member and capable of projecting from the extreme end portion of the tube, the electrode being formed of a substantially rod-shaped pliable member having flexibility;

wherein the electrode has a first portion, a second portion, and a turn portion continuously extending between the first and second portions and forming the distal end portion of the electrode, the first and second portions being intertwined with each other to form an intertwined portion and the distal end turn portion of the electrode has a diameter larger than that of the intertwined portion and smaller than that of the tube.

* * * * *